(12) United States Patent
Naidu

(10) Patent No.: US 8,299,279 B2
(45) Date of Patent: Oct. 30, 2012

(54) SEMI-SYNTHETIC PROCESS FOR THE PREPARATION OF TAXANE DERIVATIVES

(75) Inventor: Ragina Naidu, Burnaby (CA)

(73) Assignee: Chatham Biotec Ltd., Riverview, New Brunswick (CA)

( * ) Notice: Subject to any disclaimer, the term of this patent is extended or adjusted under 35 U.S.C. 154(b) by 560 days.

(21) Appl. No.: 12/524,129

(22) PCT Filed: Jan. 25, 2008

(86) PCT No.: PCT/GB2008/000280
§ 371 (c)(1),
(2), (4) Date: Jul. 22, 2009

(87) PCT Pub. No.: WO2008/090368

PCT Pub. Date: Jul. 31, 2008

(65) Prior Publication Data
US 2010/0029957 A1    Feb. 4, 2010

(30) Foreign Application Priority Data
Jan. 26, 2007   (GB) .................................. 0701523.3

(51) Int. Cl.
*C07D 311/02*    (2006.01)
*C07D 211/08*    (2006.01)
(52) U.S. Cl. ......................................  549/510; 549/511
(58) Field of Classification Search .................. 549/510, 549/511
See application file for complete search history.

(56) References Cited

U.S. PATENT DOCUMENTS

| | | |
|---|---|---|
| 4,814,470 A | 3/1989 | Colin et al. |
| 4,924,011 A | 5/1990 | Denis et al. |
| 4,924,012 A | 5/1990 | Colin et al. |
| 5,175,315 A | 12/1992 | Holton et al. |
| 5,202,448 A | 4/1993 | Carver et al. |
| 5,256,801 A | 10/1993 | Carver et al. |
| 5,449,790 A | 9/1995 | Zheng et al. |
| 5,637,739 A | 6/1997 | Jacobsen et al. |
| 6,242,614 B1 | 6/2001 | Vemishetti et al. |
| 6,281,368 B1 | 8/2001 | McChesney et al. |
| 6,410,756 B1 | 6/2002 | Zamir et al. |
| 7,358,378 B2* | 4/2008 | Vu et al. ................. 549/510 |
| 7,563,914 B2* | 7/2009 | Leze ........................ 549/510 |
| 7,906,661 B2* | 3/2011 | Naidu et al. .............. 549/510 |

(Continued)

FOREIGN PATENT DOCUMENTS

WO         WO 94/18186         8/1994

(Continued)

OTHER PUBLICATIONS

Denis, et al., "A highly efficient, practical approach to natural taxol", *J. Americ. Chem. Society*, 110(17):5917-5920 (1988). Kanazawa, et al., "Highly stereocontrolled and efficient preparation of the protected, esterification-ready docetaxel (taxotere) side chain", *J. Organic Chem.*, 59:1238-1240 (1994).
Mukaiyama, et al., "Asymmetric total synthesis of taxol" *Chemistry, A European Journal*, 5(1):121-161 (1999).

*Primary Examiner* — Andrew D Kosar
*Assistant Examiner* — Raymond Covington
(74) *Attorney, Agent, or Firm* — Pabst Patent Group LLP

(57) ABSTRACT

This invention relates to an improved semi-synthetic process for the preparation of taxane derivatives like paclitaxel, docetaxel, canadensol and its derivatives, the process, which has shorten reaction route, simple procedure, high yield and low materials cost, therefore facilitates the commercial manufacture of these derivatives.

15 Claims, 1 Drawing Sheet

U.S. PATENT DOCUMENTS

| | | |
|---|---|---|
| 2004/0132991 A1 | 7/2004 | Naidu |
| 2004/0220256 A1 | 11/2004 | Chanteloup et al. |
| 2005/0101789 A1 | 5/2005 | Naidu |
| 2005/0192445 A1 | 9/2005 | Naidu |
| 2005/0240036 A1 | 10/2005 | Naidu |
| 2005/0250954 A1 | 11/2005 | Naidu |
| 2005/0272807 A1 | 12/2005 | Naidu |
| 2007/0032646 A1 | 2/2007 | Naidu |
| 2007/0032668 A1 | 2/2007 | Naidu |
| 2007/0073069 A1 | 3/2007 | Naidu |
| 2008/0146824 A1 | 6/2008 | Naidu |

FOREIGN PATENT DOCUMENTS

| | | |
|---|---|---|
| WO | WO 99/45001 | 9/1999 |
| WO | WO 2004/033442 | 4/2004 |
| WO | WO 2005/105767 | 11/2005 |

* cited by examiner

SCHEME 1
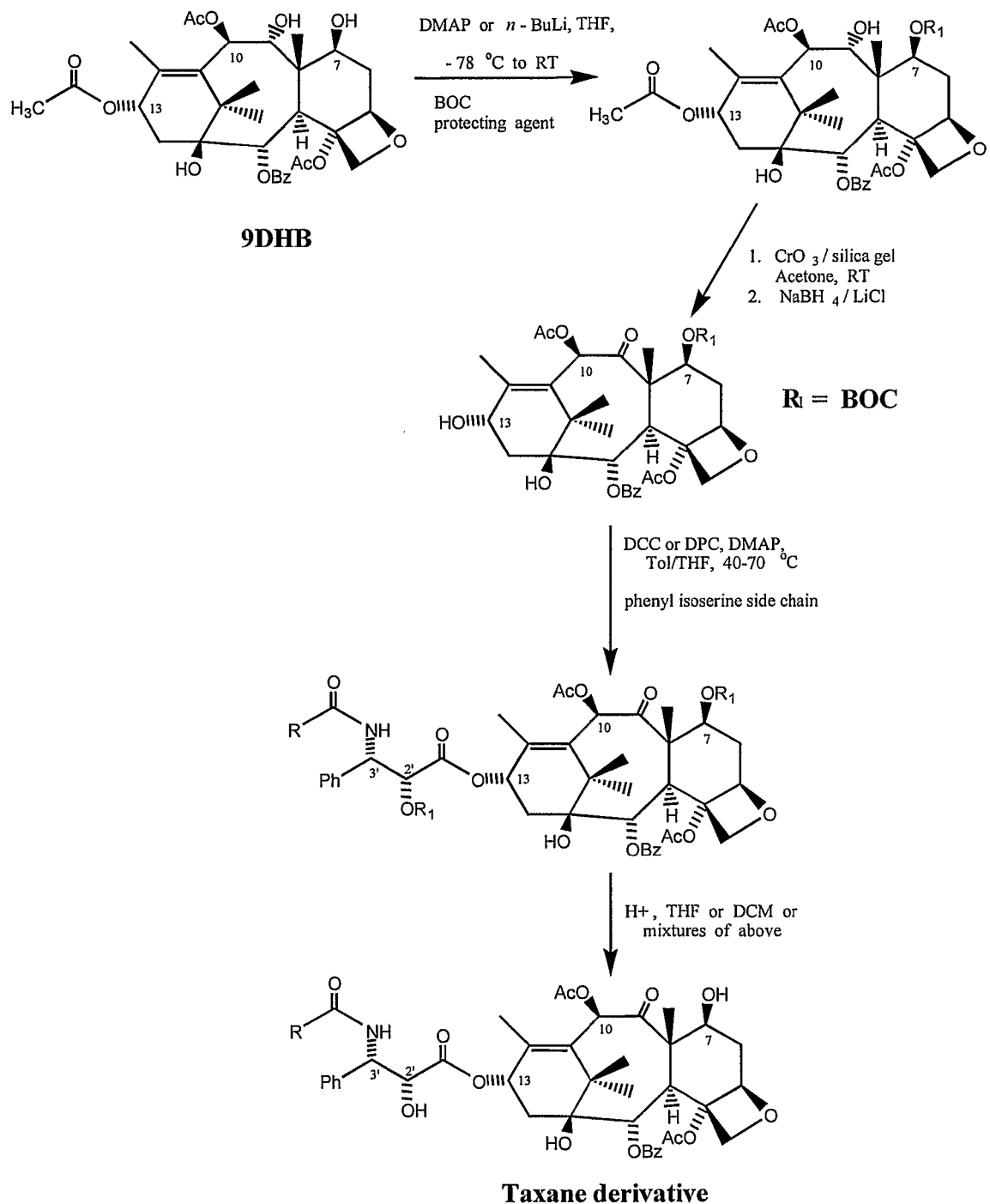
9DHB
Taxane derivative

SEMI-SYNTHETIC PROCESS FOR THE PREPARATION OF TAXANE DERIVATIVES

CROSS-REFERENCE TO RELATED APPLICATIONS

This application is a filing under 35 U.S.C. §371 of PCT/GB2008/000280, which was filed with the Great Britain Receiving Office of the Patent Cooperation Treaty on Jan. 25, 2008, which claims priority to and benefit of Great Britain Patent Application No. 0701523.3 filed on Jan. 26, 2007. The disclosures of these applications are incorporated herein by reference.

FIELD OF THE INVENTION

The present invention relates to a semi-synthetic process for the preparation of taxane derivatives like paclitaxel, docetaxel, canadensol and its derivatives.

BACKGROUND OF THE INVENTION

Description of the Related Art

The taxane family of terpenes has received much attention in the scientific and medical community, because members of this family have demonstrated broad spectrum anti-leukemic and tumor-inhibitory activity. A well-known member of this family is paclitaxel (1, Taxol®).

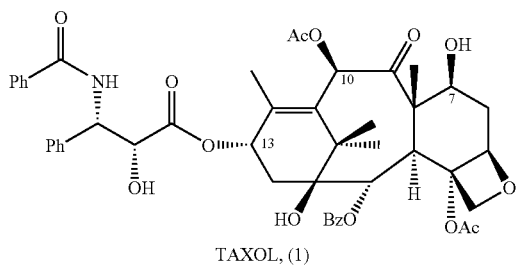

TAXOL, (1)

Paclitaxel was first isolated from the bark of the pacific yew tree (*Taxus brevifolia*) in 1971, and has proved to be a potent natural anti-cancer agent. To date, paclitaxel has been found to have activity against different forms of leukemia and against solid tumors in the breast, ovary, brain, and lung in humans.

As will be appreciated, this beneficial activity has stimulated an intense research effort over recent years with a view to identifying other taxanes having similar or improved properties, and with a view to developing synthetic pathways for making these taxanes, such as paclitaxel.

This research effort led to the discovery of a synthetic analog of paclitaxel, namely, docetaxel (2, more commonly known as taxotere). As disclosed in U.S. Pat. No. 4,814,470, taxotere has been found to have a very good anti-tumor activity and better bio-availability than paclitaxel. Taxotere is similar in structure to paclitaxel, having t-butoxycarbonyl instead of benzoyl on the amino group at the 3' position, and a hydroxy group instead of the acetoxy group at the C-10 position.

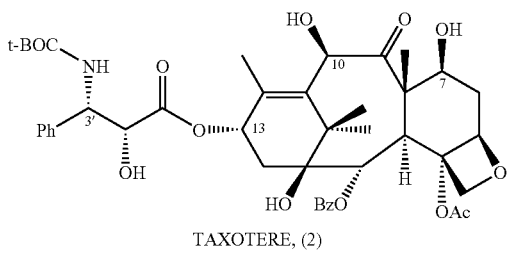

TAXOTERE, (2)

As will be appreciated, taxanes are structurally complicated molecules, and the development of commercially viable synthetic methods to make taxanes has been a challenge. A number of semi-synthetic pathways have been developed over the years, which typically begin with the isolation and purification of a naturally occurring starting material, which can be converted to a specific taxane derivative of interest. For example, paclitaxel and docetaxel may be prepared semi-synthetically from 10-deacetylbaccatin III or baccatin III as set forth in U.S. Pat. No. 4,924,011 (Denis et al.) and U.S. Pat. No. 4,924,012 (Colin et al.), or by the reaction of a beta-lactam and a suitably protected 10-deacetylbaccatin III or baccatin III derivative as set forth in U.S. Pat. No. 5,175,315 (Holton et al.) or U.S. patent application Ser. No. 10/683,865, which application is assigned to the assignee of the present invention.

Another important taxane derivative is Canadensol (2.1) and its derivatives. These can be prepared as described in U.S. Pat. No. 6,410,756 B1 (Zamir et al.).

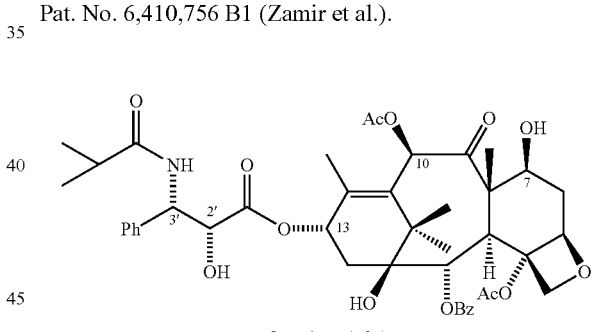

Canadensol, 2.1

The precursors or starting material, 10-deacetylbaccatin III (10-DAB, 3) and baccatin III (BACC III, 4) can be separated from mixtures extracted from natural sources such as the needles, stems, bark or heartwood of numerous *Taxus* species and have the following structures:

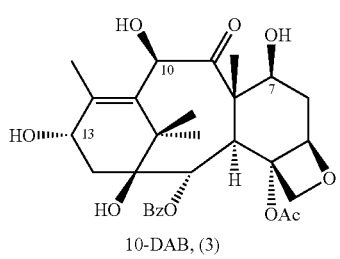

10-DAB, (3)

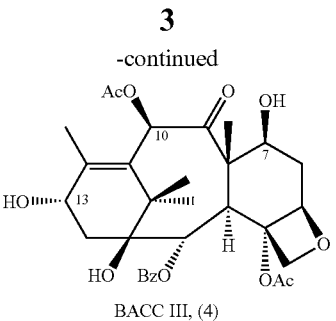

BACC III, (4)

Although much of the research towards the semi-synthesis of paclitaxel and taxotere has involved the use of 10-deacetylbaccatin III as the starting material, other taxanes from the *Taxus* species, such as 9-dihydro-13-acetylbaccatin III (9-DHB, 5), present in the Canadian yew (*Taxus Canadensis*), cephalomannine (6), 10-deacetyl taxol (10-DAT, 7), 7-xylosyl taxol (8), 10-deacetyl-7-xylosyl taxol (9) and a number of 7-epi-taxanes can also be utilised as suitable starting materials, that is, due to their availability from natural sources.

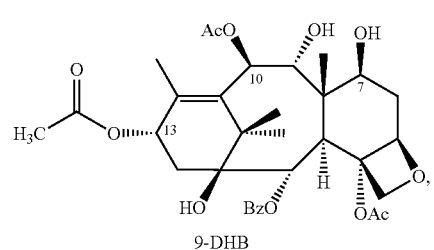

9-DHB (5)

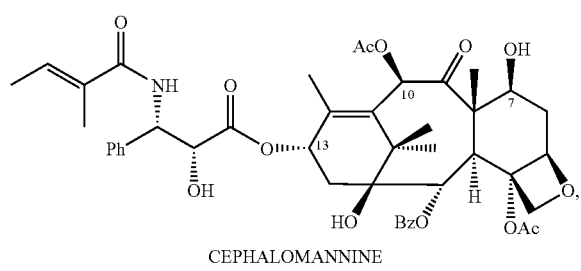

CEPHALOMANNINE (6)

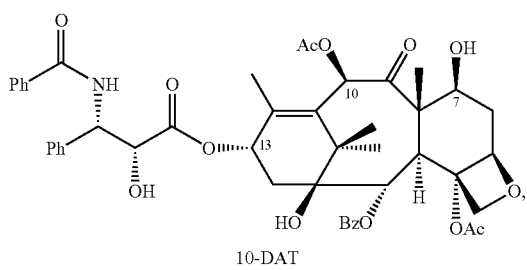

10-DAT (7)

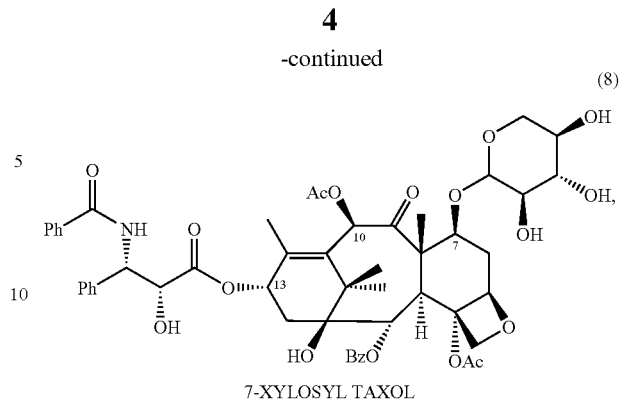

7-XYLOSYL TAXOL (8)

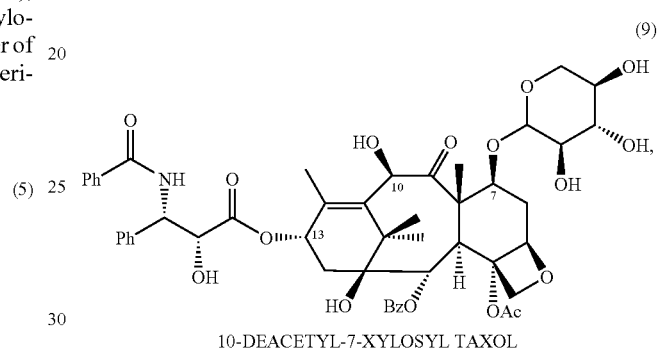

10-DEACETYL-7-XYLOSYL TAXOL (9)

In addition, U.S. Pat. Nos. 5,202,448 and 5,256,801 (Carver et al.), U.S. Pat. No. 5,449,790 (Zheng et al.) and U.S. Pat. No. 6,281,368 (McChesney et al.) disclose processes for converting certain taxanes (namely, paclitaxel, cephalomannine, 10-deacetyl taxol and certain 10-deacetyl taxol derivatives) present in partially purified taxane mixtures into 10-deacetylbaccatin III and baccatin III, which may be subsequently utilised in the foregoing semi-synthetic pathways.

As identified above, U.S. Pat. No. 4,924,011 by Denis et al. discloses a semi-synthetic process for producing paclitaxel using either baccatin III or 10-deacetylbaccatin III as a starting material. The disadvantage of the reaction process scheme advanced by Denis is it includes a long reaction pathway, it involves a complex procedure and ultimately, the yield of the protected taxane, namely, the taxane intermediate is low (only 40% in the form of a mixture of two epimers in the ratio of 60:40).

Although there have been many advances in the field, there remains a need for new and improved processes for the preparation of taxane derivatives and their conversion to paclitaxel, docetaxel, canadensol and its derivatives, and also for the preparation of taxane intermediates from crude and partially purified mixtures comprising a plurality of taxanes. It is the aim of the present invention to at least address some of the problems outlined above.

BRIEF SUMMARY OF THE INVENTION

In a first aspect of the present invention there is provided a process for producing a taxane intermediate, the process comprising the steps of: protecting the free hydroxy group at the C-7 position of a taxane of formula (I):

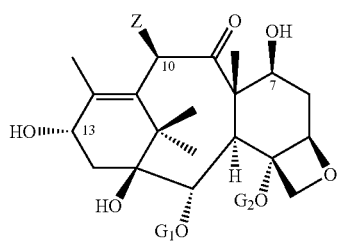

(I)

wherein, Z is —OH or a protected —OH, $G_1$ and $G_2$ are the same or different and independently a hydroxy protecting group, and attaching a side chain to the free hydroxy group at the C-13 position of the taxane of formula (I) to provide a C-13 protected taxane intermediate, characterised in that the steps of protecting and attaching comprises combining the taxane of formula (I) with a base, a suitable hydroxy protecting agent and a precursor to the side chain wherein the precursor to the side chain is a single isomer of an open chain phenylisoserine protected by a suitable hydroxy protecting agent at the 2'-position such that the resulting C-13 protected taxane intermediate has a suitable hydroxy protecting agent at the C-7 position and the 2'-position on the phenylisoserine side chain.

In brief, the present invention relates to an improved semi-synthetic process to produce a taxane intermediate, which can ultimately be used to produce taxane derivatives, such as paclitaxel, docetaxel and canadensol and its derivatives. In the process of the present invention, the protected taxane intermediate from which the taxane derivative can be derived is produced in a yield of over 65% of a single isomer by direct esterification of a protected taxane of formula (I) with a single isomeric open chain phenyl isoserine side chain. By using a single isomeric phenyl isoserine side chain, a single isomeric taxane intermediate is obtained at a yield of over 65%. This is substantially greater than the 40% yield of the process advanced by Denis et al in U.S. Pat. No. 4,924,011. In addition, by using the same hydroxyl protecting group to protect both the C-7 position and the 2'-position on the phenylisoserine side chain, simplifies and reduces the reaction route. These are all features which would be recognised as being advantageous in industrial scale up of the present process.

Preferably, the reaction is carried out at a temperature between 40-70° C. in the presence of a suitable condensing agent such as a carbodiimide, for example, dicyclohexylcarbodiimide (DCC) or a reactive carbonate, for example, di-2-pyridylcarbonate (DPC) and a catalytic amount of an activating agent such as a dialkylaminopyrimidine (DMAP), for example, 4-dimethylaminopyrimidine or similar agents. Then, after removing the protecting groups from the protected taxane intermediate with acid in THF at 30-50° C. produced the taxane derivatives such as paclitaxel or docetaxel or canadensol and its derivatives.

Preferably, the single isomer of the open chain phenylisoserine is optically active or chimeric.

Further preferably, the taxane of formula (I) is derived from at least one taxane selected from the group consisting of 10-deacetylbaccatin III, 9-dihydro-13-acetylbaccatin III.

Advantageously, the taxane of formula (I) is baccatin III.

Further preferably, the process of the present invention further includes the step of adding a hydroxy protecting agent to the 2'-position of the precursor of the side chain prior to the step of attaching the precursor to the side chain to the taxane of formula (1).

Advantageously, the hydroxy protecting agent used to protect the C-7 position and the 2'-position of the precursor of the side chain is the same or different selected from the group consisting of alkylating agents and acylating agents.

Advantageously, the hydroxy protecting agent used to protect the C-7 position and the 2'-position of the precursor of the side chain is the same or different and is selected from the group consisting of acetyl (Ac), benzyl ($PhCH_2$), 1-ethoxyethyl (EE), methoxymethyl (MOM), (methoxyethoxy)methyl (MEM), (p-methoxyphenyl)methoxymethyl (MPM), tert-butyldimethylsily (TBS), tert-butydiphenylsilyl (TBPS), tert-butoxycarbonyal (tBoc, t-Boc, tBOC, t-BOC), tetrahydrophyranyl (THP), triphenylmethyl (Trityl, Tr), 2-methoxy-2-methylpropyl, benzyloxycarbonyl (Cbz), trichloroacetyl ($OCCCl_3$), 2,2,2-trichloroethoxycarbonyl (Troc), benzyloxymethyl (BOM), tert-butyl (t-Bu), triethylsily (TES), trimethysilyl (TMS), and triisopropylsilyl (TIPS). In a particularly preferred process, the hydroxy protecting agent is tBOC. As will be appreciated, it is to be understood that the term, "hydroxy protecting agent" refers to a readily cleavable group bonded to the oxygen of a hydroxyl (—OH) group.

Further preferably, the taxane of formula (I) and the precursor to the side chain are attached by a condensation reaction carried out at a temperature of 40 to 70° C., preferably, in the presence of a mixture of toluene and tetrahydrofuran; DPC or DCC and catalytic amount of DMAP.

In a further aspect of the present invention, there is provided a process for producing a taxane derivative, the process comprising the step of de-protecting a taxane intermediate obtainable by the process of the present invention.

Advantageously, the step of de-protecting is accomplished in an acidic media, preferably formic acid, preferably, at a temperature of 30-50° C.

Preferably, the taxane derivative is paclitaxel, docetaxel, canadensol and its derivatives.

It is to be understood that the process taxane of formula (I) may be part of a mixture of taxanes comprising, in addition to the taxane of formula (I), paclitaxel, 9-dihydro-13-acetylbaccatin III, cephalomannine, 10-deacetyl taxol, 7-xylosyl taxol and 10-deacetyl-7-xylosyl taxol.

In a further aspect of the present invention there is provided, a process for preparing paclitaxel or related taxane derivatives, comprising: protecting the hydroxy group at the C-7 and/or C-10 position of a compound of formula (V):

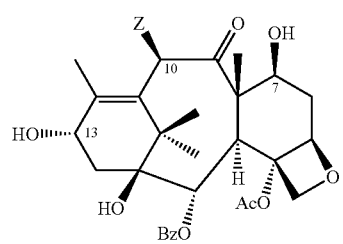

(V)

wherein, Z is —OH or protected —OH; attaching a side chain to the free hydroxyl group at C-13 position to provide a C-13 protected taxane intermediate; and converting the C-13 protected taxane intermediate to paclitaxel or related taxanes, wherein the steps of protecting and attaching comprise, contacting the compound of Formula (V) with a base, a suitable hydroxy protecting agent and a precursor to the side chain, and wherein the precursor to the side chain is a single isomer of a phenyl isoserine, preferably being protected by a hydroxyl protecting agent at the 2'-position.

The preferred features above are equally applicable mutatis mutandis to this further aspect.

As will be appreciated, the semi-synthetic process of the present invention has the following advantages:

1. The reaction route is shorter compared with the above mentioned synthetic processes. The protection of the hydroxy group is the same and all operations of this process are simple.

2. The overall yield is high. The amount of feed stock will be reduced so that economic benefits are quite considerable.

3. The monitor and control of the end point for coupling is readily facilitated.

4. Single isomeric taxane intermediate is obtained and converted to the taxane derivatives such as paclitaxel or docetaxel or canadensol, respectively.

These and other aspects of the invention will be apparent upon reference to the attached figures and following detailed description.

DETAILED DESCRIPTION OF INVENTION

One non-limiting embodiment of a process for producing a taxane intermediate and then a taxane derivative in accordance with the present invention will be exemplified by way of reference to the generalised scheme 1 of FIG. 1. In particular, the following non-limiting example discloses a representative process for synthesizing a C-13 protected taxane intermediate from 9-DHB, and the subsequent conversion of such intermediate to a taxane derivative such as paclitaxel or docetaxel or canadensol.

Unless otherwise stated, all scientific and technical terms have the meanings as understood by one of ordinary skill in the art.

A) Semi-Synthesis of C-7 Protected Taxane from 9-DHB

A stirred solution of 9-dihydro-13-acetylbaccatin III (9-DHB) in an organic solvent, such as THF, at room temperature under an argon atmosphere was treated with a hydroxy-protecting agent, such as $Boc_2O$, in the presence of a base, such as 4-(N,N-dimethylamino)pyridine. The reaction was stirred at this temperature for a period between 30 minutes to 1 hour until complete consumption of the starting materials, as evidenced by TLC.

The reaction was then worked up as usual, the organic phase was washed with water twice, a saturated aqueous sodium hydrogen carbonate solution and a saturated aqueous sodium chloride solution, and then dried over anhydrous sodium sulphate. Filtration and evaporation of the solvents under reduced pressure yielded a crude first C-7 protected 9-DHB derivative, which was further purified by either column chromatography or crystallization to afford a pure first C-7 protected 9-DHB derivative.

The first C-7 protected 9-DHB derivative was dissolved in anhydrous acetone at room temperature and an oxidizing agent, such as chromium (IV) oxide-silica gel, was added to the mixture. After stirring the solution for 30 min to 1 h, or until complete consumption of the starting material, at a temperature in the range of about 20 to 25° C., the reaction mixture was filtered through a pad of a filtering agent, such as silica gel or celite. Evaporation of the solvent yielded a crude second C-7 protected 13-acetylbaccatin III derivative which could be used in the following synthetic step or could be further purified by either column chromatography or crystallization to afford a pure second C-7 protected 13-acetylbaccatin III derivative.

The second C-7 protected 13-acetylbaccatin III derivative in an organic solvent, such as freshly distilled THF, was treated with a reducing agent, such as sodium borohydride in a phosphate buffer at pH 7.0 with a reducing salt at 0° C. The reaction was monitored by TLC and after the starting material was completely consumed the reaction was quenched with brine and worked up as usual. The crude C-7 protected baccatin III could be further purified by either column chromatography or crystallization to yield a pure C-7 protected taxane.

B: Attachment of A PHENYLISOSERINE Side Chain to a C-7 Protected Taxane

To a stirred solution of C-7 protected taxane, in an organic solvent, such as toluene or freshly distilled THF or pyridine or mixtures thereof or the like under argon atmosphere at room temperature was added slowly DCC or DPC followed by a 2' prime protected single isomeric phenyl isoserine side chain at once or slowly, after stirring for 5-10 minutes at room temperature, add catalytic amount of a base, such as 4-(N,N-dimethylamino)pyridine or similar bases and the solution was slowly warmed to reflux most preferably at 60 to 70° C., for 6-24 hrs or until most of the starting material was consumed, as evidenced by TLC. After cooling the solution, ethyl acetate was added and the mixture was then partitioned between saturated aqueous sodium hydrogen carbonate and ethyl acetate or mixtures of dichloromethane and ethyl acetate. Evaporation of the organic layer yielded the crude coupled protected taxane intermediate, which could be further purified by either column chromatography or crystallization to yield a pure C-13 protected taxane intermediate in which the resulting taxane intermediate has a suitable hydroxyl protecting agent at the C-7 position and the 2'-position on the phenyl isoserine side chain, in this case, BOC; or used directly for the next step.

C: Deprotection of the Taxane Intermediate

The C-13 protected taxane intermediate, was hydrolyzed using formic acid to remove the C-7 and C-2' protected hydroxyl groups to produce the taxane derivatives such as paclitaxel or docetaxel or canadensol or as described in U.S. patent application Ser. No. 10/790,622, which application is assigned to the assignee of the present invention and is incorporated herein by reference in its entirety.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the scope of the invention, which is not limited except as by the appended claims.

The invention claimed is:

1. A process for producing a taxane derivative, the process comprising the steps of:
protecting the free hydroxy group at the C-7 position of a taxane of formula (I):

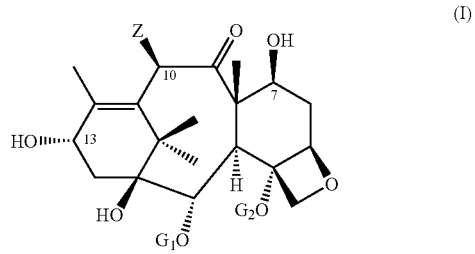

wherein, Z is —OH or a protected —OH, $G_1$ and $G_2$ are the same or different and independently a hydroxy protecting group, and attaching a side chain to the free hydroxy group at the C-13 position of the taxane of formula (I) to provide a C-13 protected taxane intermediate, wherein the steps of protecting and attaching comprise combining the taxane of formula (I) with a first base, a suitable hydroxy protecting agent and a precursor to the side chain wherein the precursor to the side chain is a single isomer of an open chain phenylisoserine protected by a suitable hydroxy protecting agent at the 2'-position such that the resulting C-13 protected taxane intermediate has a suitable hydroxy protecting agent at the C-7 position and the 2'-position on the phenylisoserine side chain, and wherein the taxane of formula (I) and the precursor to the side chain are attached by a condensation reaction carried out at a temperature of 40 to 70° C. in the presence of a mixture of toluene and tetrahydrofuran, a carbodiimide condensing agent, and a catalytic amount of a second base, such that the resulting C-13 protected taxane intermediate has a suitable hydroxyl protecting agent at the C-7 position and the 2'-position on the phenylisoserine side chain.

2. The process according to claim 1, wherein the single isomer of the open chain phenylisoserine is optically active or chimeric.

3. The process according to claim 1, wherein the taxane of formula (I) is derived from at least one taxane selected from the group consisting of 10-deacetylbaccatin III, 9-dihydro-13-acetylbaccatin III.

4. The process of claim 1, wherein the taxane of formula (I) is baccatin III.

5. The process of claim 1, further comprising adding a hydroxy protecting agent to the 2'-position of the precursor of the side chain prior to attaching the precursor to the side chain to the taxane of formula (1).

6. The process of claim 1, wherein the hydroxy protecting agent used to protect the C-7 position and the 2'-position of the precursor of the side chain is the same or different, and is selected from the group consisting of alkylating agents and acylating agents.

7. The process of claim 1, wherein the hydroxy protecting agent used to protect the C-7 position and the 2'-position of the precursor of the side chain is the same or different, and is selected from the group consisting of acetyl (Ac), benzyl ($PhCH_2$), 1-ethoxyethyl (EE), methoxymethyl (MOM), (methoxyethoxy)methyl (MEM), (p-methoxyphenyl)methoxymethyl (MPM), tert-butyldimethylsily (TBS), tert-butyldiphenylsilyl (TBPS), tert-butoxycarbonyal (tBoc, t-Boc, tBOC, t-BOC), tetrahydrophyranyl (THP), triphenylmethyl (Trityl, Tr), 2-methoxy-2-methylpropyl, benzyloxycarbonvl (Cbz), trichloroacetyl ($OCCCl_3$), 2,2,2-trichloroethoxycarbonyl (Troc), benzyloxymethyl (BOM), tert-butyl (t-Bu), triethylsily (TES), trimethysilyl (TMS), and triisopropylsilyl (TIPS).

8. The process of claim 7, wherein the hydroxy protecting agent is tBOC.

9. The process of claim 1, wherein the carbodiimide condensing agent is selected from the group consisting of di-2-pyridylcarbonate (DPC) and dicyclohexylcarbodiimide (DCC).

10. The process of claim 1, wherein the taxane of formula (I) is part of a mixture of taxanes comprising, in addition to the taxane of formula (I), paclitaxel, 9-dihydro-13-acetylbaccatin III, cephalomannine, 10-deacetyl taxol, 7-xylosyl taxol and 10-deacetyl-7-xylosyl taxol.

11. The process of claim 1, further comprising de-protecting the taxane intermediate.

12. The process of claim 11, wherein the step of de-protecting is accomplished in an acidic media at a temperature of 30-50° C.

13. The process of claim 11, wherein the taxane derivative is paclitaxel, docetaxel, canadensol and is derivatives.

14. The process of claim 1, wherein the second base is 4-(N,N-dimethylamino)pyridine.

15. The process of claim 12, wherein the acidic media comprises formic acid.

* * * * *